(12) United States Patent
Delansorne (10) Patent No.: US 9,314,474 B2
(45) Date of Patent: Apr. 19, 2016

(54) FORMULATIONS OF 14-EPI-ANALOGUES OF VITAMIN D

(75) Inventor: Remi Delansorne, Paris (FR)

(73) Assignee: HYBRIGENICS, SA, Paris (FR)

( * ) Notice: Subject to any disclaimer, the term of this patent is extended or adjusted under 35 U.S.C. 154(b) by 59 days.

(21) Appl. No.: 13/182,239

(22) Filed: Jul. 13, 2011

(65) Prior Publication Data

US 2012/0015914 A1    Jan. 19, 2012

Related U.S. Application Data

(63) Continuation of application No. 12/836,974, filed on Jul. 15, 2010.

(30) Foreign Application Priority Data

Jul. 15, 2010   (EP) .................................... 10305783

(51) Int. Cl.
| | |
|---|---|
| *A61K 31/59* | (2006.01) |
| *A61P 35/00* | (2006.01) |
| *A61P 25/00* | (2006.01) |
| *A61P 3/10* | (2006.01) |
| *A61P 17/06* | (2006.01) |
| *A61P 19/10* | (2006.01) |
| *A61K 9/08* | (2006.01) |
| *A61K 9/20* | (2006.01) |
| *A61K 9/48* | (2006.01) |
| *A61K 47/10* | (2006.01) |

(52) U.S. Cl.
CPC . *A61K 31/59* (2013.01); *A61K 9/08* (2013.01); *A61K 9/2054* (2013.01); *A61K 9/4858* (2013.01); *A61K 47/10* (2013.01)

(58) Field of Classification Search
CPC ......... A61K 31/59; A61K 9/08; A61K 47/10; A61K 9/2054; A61K 9/4858
USPC ........................................................ 514/167
See application file for complete search history.

(56) References Cited

U.S. PATENT DOCUMENTS

| | | | |
|---|---|---|---|
| 6,706,725 B1 * | 3/2004 | Bernardon ..................... | 514/277 |
| 7,067,154 B1 * | 6/2006 | Valleri et al. .................... | 424/501 |
| 2002/0006443 A1 * | 1/2002 | Curatolo et al. ............... | 424/486 |
| 2005/0020546 A1 | 1/2005 | Laidlaw et al. | |
| 2006/0189576 A1 * | 8/2006 | Bouillon et al. ................ | 514/63 |
| 2007/0093458 A1 | 4/2007 | Schwartz et al. | |
| 2008/0145411 A1 | 6/2008 | Shinagawa et al. | |
| 2010/0278784 A1 | 11/2010 | Pojasek et al. | |
| 2010/0330156 A1 * | 12/2010 | Liu et al. ........................ | 424/450 |

FOREIGN PATENT DOCUMENTS

| | | |
|---|---|---|
| EA | 002492 B1 | 6/2002 |
| EP | 0972762 A2 | 1/2000 |
| EP | 2 263 677 A1 | 12/2010 |
| EP | 2263677 | 12/2010 |
| EP | 2407154 | 1/2012 |
| EP | 2407155 | 1/2012 |
| JP | H09500117 | 2/1997 |
| JP | 2003506476 | 2/2003 |
| JP | 2003517470 | 5/2003 |
| JP | 2010 111593 A | 5/2010 |
| JP | 2010111593 | 5/2010 |
| JP | 2013531023 A | 8/2013 |
| JP | 2013531024 A | 8/2013 |
| WO | WO9501960 | 1/1995 |
| WO | WO9906051 | 2/1999 |
| WO | WO0112155 | 2/2001 |
| WO | WO0137808 | 5/2001 |
| WO | WO 2006 042383 | 4/2006 |
| WO | WO2006042383 | 4/2006 |
| WO | WO2008044659 | 4/2008 |
| WO | WO2008143928 | 11/2008 |

OTHER PUBLICATIONS

Strickley, Robert, "Solubilizing Excipients in Oral and Injectable Formulations", Pharmaceutical Research, vol. 21, No. 2, pp. 201-230(2004).
"Promising Interim Results From Hybrigenics' Inecalcitol Phase II in Combination with Taxotere(R) for Hormone-Refractory Prostate Cancer", Internet Citation, Apr. 19, 2009, pp. 1-3, XP002592440, Retrieved from the Internet: URL:http://www.medicalnewstoday.com/articles/146552.php [retrieved on Jul. 8, 2010].
Manus, et al. "Inecalcitol, traitement du cancer de la prostate", Revue Francophone Des Laboratoires, Elsevier, Amsterdam, NL, vol. 2008, No. 405, Oct. 1, 2008, pp. 12, XPO25686090.
Extended European Search report issued in EP 10305783.2-2112 dated Nov. 7, 2011.
Michael F. Holick, "Vitamin D: Important for Prevention of Osteoporosis, Cardiovascular Heart Disease, Type 1 Diabetes, Autoimmune Diseases, and Some Cancers," South. Med. J., Southern Medical Association, 2005, pp. 1024-1027.
Daniel D. Bikle, "Vitamin D: Newly Discovered Actions Require Reconsideration of Physiologic Requirements," Trends Endocrinol Metab., Jun. 2010;21(6):pp. 375-384.
Tom D. Thacher and Bart L. Clarke, "Vitamin D Insufficiency," Mayo Clin. Proc. 2011; vol. 86 (No. 1):pp. 50-60.
Behzat Özkan, "Nutritional Rickets," J. Clin. Res. Ped. Endo. 2010; vol. 2 (No. 4): pp. 137-143.
Michael F. Holick, "Resurrection of Vitamin D deficiency and Rickets," The Journal of Clinical Investigation, vol. 116, No. 8, Aug. 2006, pp. 2062-2072.
K. G. Saag and P. Geusens, "Progress in Osteoporosis and Fracture Prevention: Focus on Postmenopausal Women," Atthritis Research & Therapy 2009, vol. 11, pp. 251-269.
Caryl A. Nowson, "Prevention of Fractures in Older People with Calcium and Vitamin D," Nutrients 2010, vol. 2, pp. 975-984.
Jitsuyo Iyakuhin Tenkabutsu 1974, p. 103-120, Translation of Relevant Paragraphs, pp. 104-105, 1.1 Excipients, included.
Iyakuhin Tenkabutsu 2007, p. 67, Translation of Relevant Paragraph, pp. 67, Left column, included.
Donald L. Trump, et al. "The Anti-tumor Effects of Vitamin D in Other Cancers", Vitamin D, Third Edition, 2011, Chapter 90.

(Continued)

*Primary Examiner* — Sarah Pihonak
*Assistant Examiner* — Jason A Deck
(74) *Attorney, Agent, or Firm* — Davidson, Davidson & Kappel LLC (57) ABSTRACT

The present invention provides new formulations of 14-epi-analogues of vitamin D, such as inecalcitol, providing improved absorption profile.

35 Claims, 4 Drawing Sheets

(56) References Cited

OTHER PUBLICATIONS

Vitamin D, Third Edition, vol. 1, Table of Contents, 2011.
Donald L. Trump, et al. Vitamin D and Cancer, Table of Contents, 2011.
Declaration under Rule 132 of inventor Remi Delansorne, dated Jul. 18, 2012.
Hybrigenics, Press Release, Hybrigenics receives FDA green light for Phase II clinical study of inecalcitol in Acute Myeloid Leukemia in the United States, Paris, France, Jan. 11, 2016.
Department of Health & Human Services, May 14, 2014, Letter in response to request for orphan-drug designation of inecalcitol for "treatment of chronic lymphocytic leukemia".
Department of Health & Human Services, Aug. 3, 2015, Letter in response to request for orphan-drug designation of inecalcitol for "treatment of acute myeloid leukimia".
Japanese Office Action in corresponding Japanese Application No. 213-519093, dated May 25, 2015.
Verlinden, et al. "Two Novel 14-Epi-Analogues of 1,25-Dihydroxyvitamin D3 Inhibit the Growth of Human Breast Cancer Cells in Vitro and in Vivo" May 15, 2000. Cancer Research, vol. 60, pp. 2673-2679.
Ryoko Okamoto, et al. "Inecalcitol, an analog of $1\alpha$, 25 (OH) 2 D3, induces growth arrest of androgen-dependent prostate cancer cells" International Journal of Cancer, 2011. pp. 1-10.
Promising Interim Results From Hybrigenics' Inecalcitol Phase II in Combination With Taxotere® for Hormone-Refractory Prostate Cancer, http://www.medicalnewstoday.com/releases/146552.php , Apr. 19, 2009.
Robert G Strickley, "Solubilizing Excipients in Oral and Injectable Formulations" Pharmaceutical Research vol. 21, Issue 2, pp. 201-230. Feb. 2004.
Von Willebrand, "Inecalcitol, traitement du cancer de la prostate" Revue Française des Laboratoires, vol. 5, Sep.-Oct. 2006 (With Translation).

* cited by examiner

FORMULATIONS OF 14-EPI-ANALOGUES OF VITAMIN D

This application claims priority under 35. U.S.C. §120 to U.S. Pat. application Ser. No. 12/836,974, filed Jul. 15, 2010, and claims priority under 35 U.S.C. §199 to European Patent Application 10305783.2, the entire disclosures of which are hereby incorporated by reference.

FIELD OF THE INVENTION

The present invention concerns improved formulations of 14-epi-analogues of vitamin D.

BACKGROUND

Vitamin D belongs to the group of fat-soluble vitamins, together with vitamins A, E and K. The two main natural forms of vitamin D: vitamin $D_2$ (also named ergocalciferol) and vitamine $D_3$ (also named cholecalciferol) are soluble in lipids and insoluble in water, like all their chemical derivatives.

Vitamin D, its metabolites and analogues have potent effects on calcium and phosphate metabolism and can therefore be used for prevention and therapy of vitamin D deficiency, such as rickets and other disorders of plasma and bone mineral homeostasis such as osteoporosis and osteomalacia. Moreover, vitamin D receptors and vitamin D activity have also been documented in numerous other tissues and cells, where they are also known to be involved in cell proliferation and differentiation. Vitamin D also affects the immune system as vitamin D receptors are expressed in several white blood cells including monocytes, macrophages and T and B lymphocytes.

Pharmaceutical formulations of vitamin D compounds as active pharmaceutical ingredients show a large variety: ergocalciferol is available in solution in ethanol for oral administration or in arachis oil for injection since 1940; cholecalciferol is marketed as a solution in medium-chain triglycerides (MCT) both for oral and injectable administrations since 1964; in 1974, a droplet formulation of calcifediol (25-hydroxy-cholecalciferol) in solution in propylene glycol was introduced; in 1979, alfacalcidol (1-hydroxy-cholecalciferol) was approved for oral administration as soft gelatin capsules filled with solution in sesame oil; in 1982, calcitriol (1,25-dihydroxy-cholecalciferol) was launched in soft gelatin capsules filled with solution in MCT; in 1989, a new formulation of cholecalciferol was made available as drinking solution in a complex mixture of polyoxyethylenated glycerides, propylene glycol, glycerol, Cremophor EL and phosphate buffer; in the same year, a new formulation of ergocalciferol was also marketed in a complex mixture of polyoxyethyletaned and glycosylated glycerides; in 2000, a new simple solution of cholecalciferol in olive oil was introduced as a drinking solution; the two latest innovative vitamin D compounds to have been approved for oral pharmaceutical use, doxercalciferol in 1999 and paricalcitol in 2005, are both formulated as solution in MCT in soft gelatin capsules; finally, elocalcitol has recently been developed up to phase IIb clinical trials in soft gelatin capsules containing MCT (U.S. Pat. No. 7,332,482).

The absorption of cholecalciferol has been compared when given to human volunteers in solution in identical soft gelatin capsules containing either arachis oil or MCT (Miglyol 812®): in the fasting state, bioavailability of cholecalciferol was about twice higher from arachis oil capsules than from MCT capsules (Holumberg et al., 1990, Biopharm. Drug Disp., 11, 807-8015). When given with a standard meal, no difference was observed.

The bioavailability of seocalcitol, a cholecalciferol derivative, was studied in rats in solution either in propylene glycol as the reference formulation, or in two types of lipids: MCT or long chain triglycerides (LCT) (Grove et al., 2005, J. Pharm. Sci., 8, 1830-1838). A two-fold increase in bioavailability of seocalcitol was demonstrated in both lipid formulations over the reference solution in propylene-glycol; no difference was observed between the LCT- or MCT-based formulations.

The optimization of the oral delivery of lipophilic compounds in lipid-based formulations has been reviewed (Porter et al., Nature Rev. Drug Discovery, 2007, 6, 231-248). Differences between MCT and LCT on different mechanisms involved in the efficiency of lipophilic drug bioavailability were listed such as drug solubilisation, reduction in gastrointestinal motility, lymphatic versus hepatic portal transport, secretion of biliary salts and of endogenous phospholipids, or the dynamics of lamellar versus cubic liquid crystal phases in the course of lipid droplet digestion into vesicles, mixed micelles and simple micelles.

The complexity of lipid drug absorption has sometimes led to complex formulations incorporating several components playing several different roles such as solvent, surfactant, co-solvent, co-surfactant and the like. Such a complex system has been tested with seocalcitol without any improvement in bioavailability as compared with simple solutions in MCT or LCT (Grove et al., 2006, Eur. J. Pharma. Sci., 28, 233-242).

In summary, "the choice of specific formulation components to provide optimal pharmaceutical and biopharmaceutical properties is drug specific and will depend on drug dose and the physicochemical properties of the compound concerned" (Porter et al., ibid, 2007, page 239, box 3). This explains the variety of oral formulations for the variety of vitamin D compounds, although soft gelatin capsules appear to be the most popular galenic form and MCT the most frequent excipient.

On the other hand, these so-called non-calcemic effects of vitamin D lead to consider the possible use of vitamin D derivatives for various therapeutic applications such as disorders of the immune system, hormone secretion, cell differentiation or cell proliferation. In particular, such compounds may be useful in the therapy of disorders characterized by increased cell proliferation, such as psoriasis and/or cancer. In particular, $1,25(OH)_2$-vitamin $D_3$, the active metabolite of vitamin $D_3$ named calcitriol, is known to inhibit the proliferation of many cancer cells lines of various origins in vitro and to slow the progression of various tumor xenografts in vivo.

A large number of analogues of calcitriol displaying a clear dissociation between anti-proliferative and calcemic effects have been reported. In particular, EP 0 707 566 B1 discloses a number of calcitriol analogues such as 14-epi-analogues. Among these 14-epi-analogues of calcitriol is inecalcitol of formula:

Inecalcitol is the international non-proprietary name for 19-nor-9,10-seco-14βH-cholesta-5(Z),7(E)-dien-23-ino-1α, 3β,25-triol-23-yne ($C_{26}H_{40}O_3$).

Inecalcitol is a synthetic derivative of calcitriol, the natural active metabolite of vitamin $D_3$. Eelen et al. (*Molecular Pharmacology* 67, 1566-1573, 2005) and Verlinden et al. (*Journal of Bone and Mineral Research*, volume 16(4), 625-638, 2001) showed the enhanced antiproliferative and markedly lower calcemic effects of inecalcitol compared with calcitriol.

Inecalcitol is an original vitamin D analogue different from all other vitamin D derivatives by the cis conformation of the junction between the C and D rings of the molecule, rather than the trans configuration in the natural vitamin D compounds (Verlinden et al., 2000, *Cancer Res.*, 60. 2673-2679). This modification, also called 14-epimerization, has been described for the first time by Maynard et al. (1994, *J. Med. Chem.*, 37, 2387-2393) in the vitamin D series, and only very seldom applied to synthesize new 14-epi-vitamin D analogues (WO 2004 080922 and related patent documents; U.S. Pat. No. 5,936,105; WO 95/01960 and related patent documents; Sawada et al., 2009, *Bioorg. Med. Chem.*, 19, 5397-5400; Sawada et al., 2009, *Chem. Pharm. Bull*, 57, 1431-1433; Kittaka et al., 2009, *Anticancer Res.*, 9, 3563-3569. Sawada et al.; 2010, J. Steroid Biochem. Mol Biol., doi: 10.1016/j.jsbmb.2010.02.035). Inecalcitol is the most advanced 14-epi vitamin D derivative in terms of clinical development: it has been tested both in healthy volunteers and in human patients by oral administration in the classical formulation as a solution in MCT in soft gelatin capsules, like elocalcitol, paricalcitol, doxercalciferol, calcitriol and the first formulation of cholecalciferol.

A major feature of inecalcitol profile is its very low calcemic activity, especially in monkeys and human subjects, allowing the oral administration of very high doses. In humans, the maximal tolerated (MDT) dose is 4 mg per day, much higher than the MTD of any other vitamin D analogue previously determined: 10 μg per day for seocalcitol, 45 μg once a week for calcitriol and 150 μg per day for elocalcitol.

Thus, inecalcitol, as a representative of a unique physicochemical class of 14-epi-derivatives of vitamin D, also differs for the range of dose at which it can be administrated. Both reasons may explain the unpredictable results obtained with high dose formulations of inecalcitol orally administrated to monkeys as test animals, more representative of human tolerance than rats.

SUMMARY OF THE INVENTION

In view of the unique structure and doses, the usual formulations of vitamin D derivatives may not be optimized for the 14-epi-analogues. It is thus desirable to provide improved formulations of 14-epi-analogues of vitamin D, in particular inecalcitol.

It is an object of the present invention to provide new oral formulations of 14-epi-analogues of vitamin D, such as inecalcitol, showing an improved absorption profile over the Medium Chain Triglycerides (MCT) formulation of said 14-epi-analogues of vitamin D, in particular in terms of the peak concentration (Cmax).

Preferably, the formulations of the invention exhibit at least two-fold increase of the Cmax peak of the MCT formulation in mammals, such as in human and/or monkeys.

The formulations of the invention may also exhibit additionally or alternatively an improved overall bioavailability ($AUC_{0-24h}$) over the Medium Chain Triglycerides formulation of said 14-epi-analogues of vitamin D. Preferably, the formulations of the invention lead to a higher $AUC_{0-24h}$ than the Medium Chain Triglycerides formulation of said 14-epi-analogues of vitamin D in mammals, such as in human and/or monkeys.

According to a first object, the present invention concerns an oral formulation of a 14-epi-analogue of vitamin D characterized by an improved absorption profile over the Medium Chain Triglycerides (MCT) formulation of said 14-epi-analogues of vitamin D.

According to a second object, the present invention also concerns an oral formulation of a 14-epi-analogue of vitamin D for use for improving the absorption of said 14-epi-analogue over the formulation in medium chain triglycerides.

The improved absorption profile is such that the oral formulations of the invention have a higher peak concentration (Cmax) and may additionally exhibit a higher overall absorption ($AUC_{0-24h}$) than the corresponding formulation in MCT of said 14-epi-analogue of vitamin D.

As used herein, the terms "14-epi-analogue of vitamin ID" refers to analogues of vitamin D derivatives, such as ergocalciferol, cholecalciferol, calcifediol, alfacalcidol, elocalcitol, seocalcitol, paricalcitol, doxercalciferol, calcitriol and the like, which further have a cis CID configuration. This includes in particular inecalcitol.

In the oral formulations of the invention, the concentration of said 14-epi-analogue in said formulation is comprised between 0.001 and 50% (weight).

The oral formulations of the invention may be in the form of a dry formulation, a soft gelatin capsule or a solution, as follows.

According to a first embodiment, the oral formulation of the invention may be in the form of a dry formulation which comprises:
  at least one 14-epi-analogue of vitamin D,
  carboxymethylcellulose (CMC),
and one or more optional pharmaceutically acceptable excipient(s).

Generally, the oral formulation of the invention comprises between 0.1 and 50% (weight) of CMC. In particular, it has been surprisingly discovered that dry formulations of 14-epi-analogues of vitamin D with CMC lead to an improved absorption over the corresponding MCI formulations of said 14-epi-analogues. This result is unexpected as vitamin D analogues have always been consistently formulated in a lipid-based medium such as oils.

Figure 4:
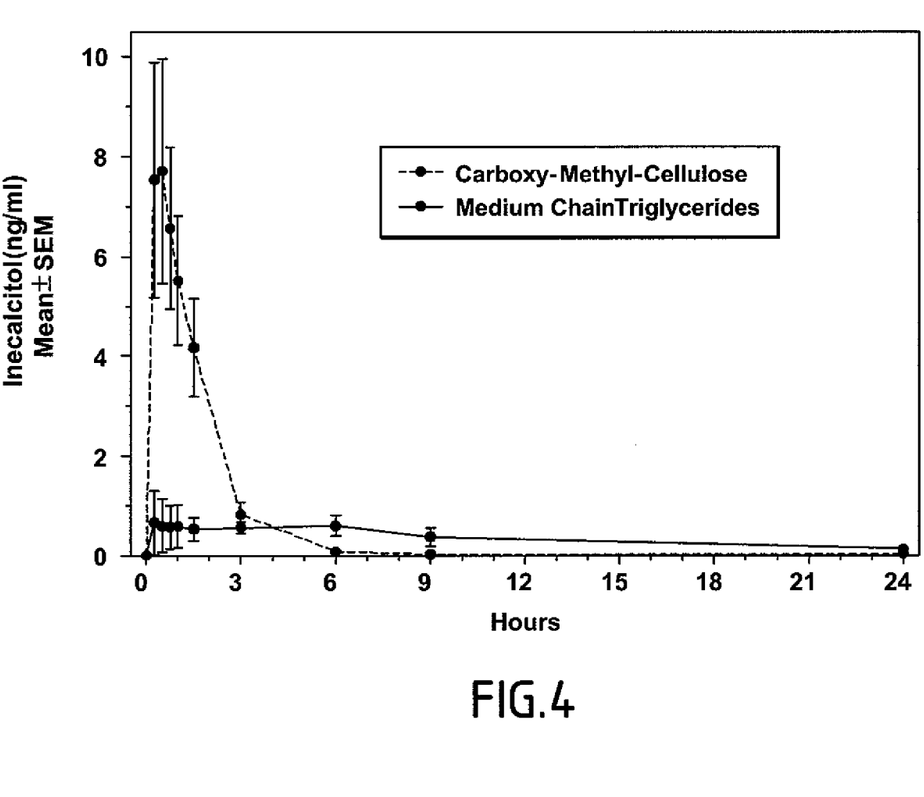
FIG. 4 shows the time-dependent concentration of inecalcitol following its oral administration with CMC in monkeys.

Specifically, it was shown that when inecalcitol was administered to monkeys in suspension in a water solution of the hydrophilic linking/disintegrating excipient CMC, the absorption was better than from any solution of inecalcitol in any lipid-based excipient. Peak concentration was almost 12-fold higher with suspensions in CMC solutions than with solution in MCT. The overall bioavailability was increased by 66% as illustrated in FIG. 4.

Dry forms include tablets, pills, powders, hard capsules, pastilles, troches, lozenges and the like. They can contain one or more of any of the following ingredients, or compounds of a similar nature: a binder such as microcrystalline cellulose, cellulose derivatives, gelatin, starch, pregelatinized starch, pyrrolidone, polyvinylpyrrolidone, xanthan gum, or tragacanth gum; a diluent such as powdered sugar, calcium salts, mannitol, sorbitol, kaolin, starch or lactose; a disintegrant such as starch, crospovidone, maltodextrins and cellulose derivatives; a lubricant such as magnesium stearate, calcium stearate, stearic acid, or vegetable oil; a glidant such as talc or colloidal silicon dioxide; an antioxidant such as ascorbic acid, sodium ascorbate, citric acid, tocopherols, alpha-tocopherol or alpha-tocopheryl acetate; a sweetening agent such as sucrose or saccharin; or a flavoring agent such as peppermint, or glycocholate methyl salicylate.

Preferred tablets may contain one or more of carboxymethylcellulose, microcrystalline cellulose, lactose, colloidal silicon dioxide, cornstarch, pregelatinized starch, povidone, crospovidone, maltodextrins, magnesium stearate, alpha-tocopheryl acetate or alpha-tocopherol in any combination.

Additionally, the tablets can be coated for improved long-term stability, for protection against gastric degradation or for controlled or programmed release. The coating is generally achieved with a solution of film forming polymers such as polyvinylic alcohol, polyethylene glycol, cellulose derivatives (esters, ethers or aliphatic substitutions) or acrylic derivatives. The coating can also include pharmaceutically acceptable dyes such as iron oxides, and fillers such as titanium dioxide or talc. Preferred coatings for tablets contain one or more of polyvinylic alcohol, polyethylene glycol of various molecular weights, titanium dioxide and talc.

According to a second aspect, the oral formulations of the invention may be in the form of a soft gelatin capsule comprising:
    at least one 14-epi-analogue of vitamin ID,
    at least one Long Chain Triglyceride (LCT),
and one or more optional pharmaceutically acceptable excipient(s).

Generally, in the oral formulation, the concentration (weight) of LCT is comprised between 1% and qsp.

It has also been surprisingly discovered that formulations of 14-epi-analogues with Long Chain Triglycerides (LCT) lead to an improved absorption over the corresponding MCT formulations of said 14-epi-analogues. This result is unexpected as this improved activity is not obtained with non esterified corresponding long-chain fatty acid like oleic acid.

The terms "Long Chain Triglyceride" refer to long chains comprising more than 14 carbon atoms fatty esters of glycerol. Preferably they comprise 15 to 24 carbon atoms. Long Chain Triglyceride may be chosen from vegetable oils such as arachis oil, olive oil, sunflower oil, canola, cottonseed, corn, linseed, palm, rapeseed, sesame, soybean and their main constituents: glycerol fully esterified with stearic acid, oleic acid, linoleic acid, linolenic acid, eicosanoic acid, eicosenoic acid, behenic acid, erucic acid, tetracosanoic acid, palmitic acid, palmitoleic acid, margaric acid or margaroleic acid or pentadecanoic acid, and their derivatives. Preferred LCT are olive, arachis or sunflower oils, and their mixtures.

By contrast, MCT refers to Medium-chain triglycerides (MCTs), comprising 6 to 14 carbons fatty acid esters of glycerol: caproic acid, caprylic acid, capric acid, lauric acid, myristic acidor myristoleic acid, and their derivatives MCT are found in vegetable oils such as coconut oil or palm kernel oil.

Figure 1:
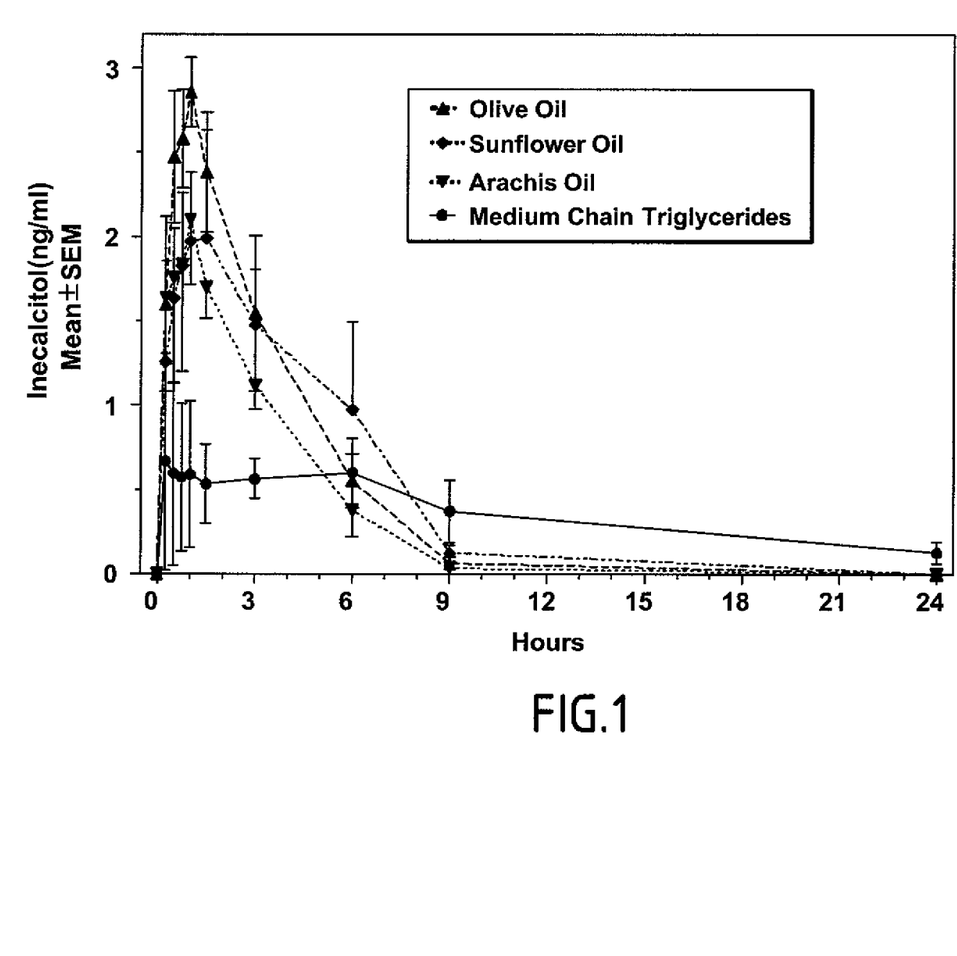
FIG. 1 shows the time-dependent concentration of inecalcitol following its oral administration in LCT (olive oil, sunflower oil and arachis oil) or in MCT in monkeys.

Specifically, inecalcitol was better absorbed from LCT (arachis oil, sunflower oil, olive oil) than from MCT as apparent from the results illustrated in FIG. 1.

Figure 2:
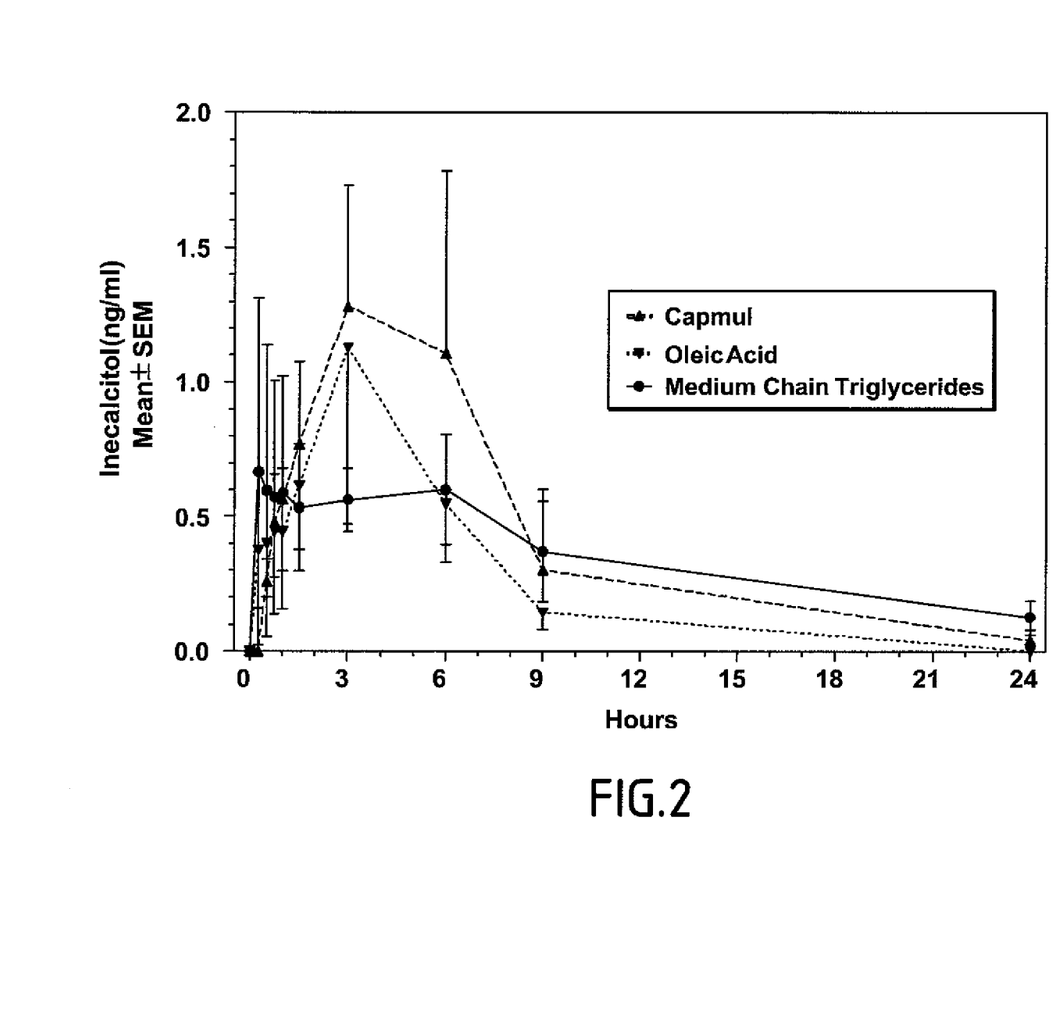
FIG. 2 shows the time-dependent concentration of inecalcitol following its oral administration with capmul, oleic acid or MCT in monkeys, for comparative purposes.

Long-chain fatty acid like oleic acid, the majority fatty acid esterified in the olive oil triglycerides, changed the course of inecalcitol absorption by delaying and slightly increasing its peak concentration, but reduced its overall bioavailability, as illustrated in FIG. 2.

Soft gelatin capsules are made from gelatin blends, optionally blended with plasticizers such as glycerol, glycerin, sorbitol and sorbitol derivatives. Soft gelatin capsules can be filled with various solutions or emulsions of pharmaceutically active ingredient in LCT alone or mixed with other excipients like surfactants such as polyethyleneglycerides, polysorbates, hydrogenated castor oil and the like, emulsifyers such as phospholipids, semi-synthetic mono-or di-glycerides, propylene glycol, esters of propylene glycol, esters of fatty acids, cholesterol derivatives, lecithins, and the like, or antioxydants such as butylhydroxyanisole, butylhydroxytoluene, ascorbic acid, citric acid, tocopherols or alpha-tocopherol, and the like.

According to a third aspect, the oral formulations of the invention may be in the form of a solution comprising:
    at least one 14-epi-analogue of vitamin D,
    propylene glycol,
and one or more optional pharmaceutically acceptable excipient(s).

Generally, in the oral formulations of the invention, the concentration (weight) of propylene glycol is comprised between 1% and qsp.

It has further been surprisingly discovered that solutions of 14-epi-analogues of vitamin D in propylene glycol also lead to an improved absorption over the corresponding MCT formulations of said 14-epi-analogues. This result is unexpected as this improved activity is not obtained with the monoester of propylene glycol with caprylic acid (CapmulPG8®).

Figure 3:
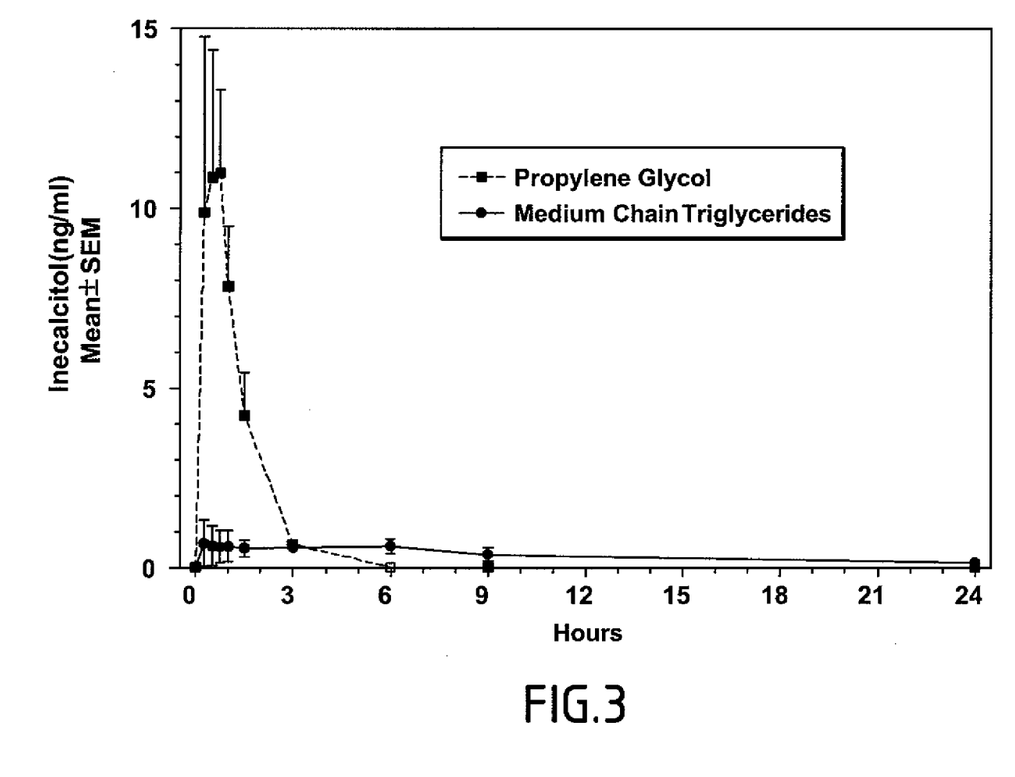
FIG. 3 shows the time-dependent concentration of inecalcitol following its oral administration with propylene glycol in monkeys.

Specifically, inecalcitol was better absorbed from propylene glycol (e.g. to give rise to peak values more than 15-fold higher and to total bioavailability nearly doubled, in monkeys) than from in MCT. These results are illustrated in FIG. 3. However, the monoester of propylene glycol with caprylic acid (CapmulPG8®) increased inecalcitol peak plasma concentration only by a factor less than 2, for an increase in bioavailability limited to about 20% as apparent from FIG. 2.

Propylene glycol formulations may additionally comprise water at a concentration of from 0 to 98.009%.

Solutions of the invention may be in the form of syrup or elixir. They may contain sweetening agents, preservatives, dyes, colorings, and flavorings.

The liquid compositions may also include binders, buffers, preservatives, chelating agents, sweetening, flavoring and coloring agents, and the like.

Formulations include a flavored base, such as sucrose or acacia, and other excipients such as glycocholate.

"Qsp" is used herein to indicate that the ingredient is present in the oral formulation in an amount necessary and/or sufficient to achieve the desired final weight of said formulation. It is thus used to refer to the complementary part or balance quantity of said ingredient.

The oral formulations of the invention may be in the form of a unit dose. Such unit doses generally comprise from 0.5 to 20 mg of said 14-epi-analogue.

The oral formulations are suitable for use in the prevention and/or treatment of rickets, osteoporosis, osteomalacia, psoriasis, autoimmune diseases such as multiple sclerosis or type I diabetes, hyperparathyroidism, benign prostate hyperplasia, any type of cancer or any vitamin D associated disease.

According to a further object, the present invention concerns a method for treating and/or preventing rickets, osteoporosis, osteomalacia, psoriasis, autoimmune diseases such as multiple sclerosis or type I diabetes, hyperparathyroidism, benign prostate hyperplasia, any type of cancer or any vitamin D associated disease, in particular cancer, comprising administering a formulation of the invention to a human or animal patient in need thereof.

The formulations of the invention may provide any therapeutically effective amount of said 14-epi-analogue. The administration dose of said 14-epi-analogue is preferably comprised between 1.5 mg and 20 mg.

The method of the invention advantageously does not induce increased calcemia in the treated patient.

The method of the invention may comprise the administration of said doses of the 14-epi-analogue, at a frequency comprised between every three days up to three times a day, such as every three days, every other day (qod), once-a-day (qd), twice-a-day (bid) or three times a day (tid). Preferably, the administration may take place every other day, once a day or twice-a-day.

DETAILED DESCRIPTION

As used herein, a "therapeutically effective amount" refers to an amount of a 14-epi-analogue which is effective in preventing, reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment. The identification of those subjects who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a 14-epi-analogue, which is required to achieve the desired biological effect, will vary depending upon a number of factors, including the chemical characteristics (e.g. hydrophobicity) of the compounds employed, the potency of the compounds, the type of disease, the species to which the patient belongs, the diseased state of the patient, the route of administration, the bioavailability of the compound by the chosen route, all factors which dictate the required dose amounts, delivery and regimen to be administered.

In the context of the invention, the term "treating" or "treatment", as used herein, means reversing, alleviating, inhibiting the progress of, or preventing the disorder or condition to which such term applies, or one or more symptoms of such disorder or condition.

According to the invention, the terms "patient" or "patient in need thereof" are intended for an animal or a human being affected or likely to be affected with a pathological condition as discussed above. Preferably, the patient is human.

As used herein, "pharmaceutically acceptable excipient" includes any carriers, diluents, adjuvants or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients can also be incorporated into the compositions as suitable therapeutic combinations.

The formulations of the invention may be prepared by admixture of their ingredients.

The formulations may conveniently be administered in unit dosage form and may be prepared by any of the methods well-known in the pharmaceutical art, for example, as described in *Remington: The Science and Practice of Pharmacy*, $20^{th}$ ed.; Gennaro, A. R., Ed.; Lippincott Williams & Wilkins: Philadelphia, Pa., 2000.

The following examples are given for illustrative and non-limiting purpose.

EXAMPLE 1

Inecalcitol was dissolved in arachis oil, olive oil, sunflower oil (0.4 mg/ml, i.e. 0.044% w/w), propylene glycol (0.4 mg/ml, i.e. 0.039% w/w), oleic acid (0.4 mg/ml, i.e. 0.045% w/w), MCT (0.4 mg/ml, i.e. 0.042% w/w), or Capmul PG80 (0.4 mg/ml, i.e. 0.044% w/w), or dispersed as a fine milky suspension in pharmaceutical grade distilled water containing 0.5% (w/v) carboxymethylcellulose, corresponding to a 3.33% w/w concentration in the tablet formulation (5 mg CMC and 2 mg Inecalcitol in each tablet weighing 150 mg without coating). Male cynomolgus monkey received a single oral administration of a high dose of inecalcitol (2 mg/kg) in the same volume (5 ml/kg) for each excipient. Blood samples were drawn at the time of administration (To) and 15, 30, 45, 60, 90 minutes, 3, 6, 9 and 24 hours later. Plasma aliquots were prepared on heparinized tubes and unchanged inecalcitol was specifically assayed by HPLC/MS/MS method. Mean pharmacokinetic profiles (±SEM) are plotted in FIGS. 1 to 4; the mean maximum concentrations (Cmax) and area under the curve over 24 hours after administration ($AUC_{0-24h}$) were expressed in relation to the mean value observed with the reference solution of inecalcitol in MCT (Table 1); the median time (Tmax) at which Cmax was observed in the different animals receiving the same treatment was determined (Table 1).

TABLE 1

| Excipient | Cmax (-fold) | Tmax (h) | $AUC_{0-24\,h}$ (%) | N |
|---|---|---|---|---|
| MCT | 1 | 0.25 | 100 | 6 |
| Oleic acid | 1.7 | 3 | 67% | 4 |
| Capmul PG8 | 1.9 | 3 | 121% | 3 |
| *Arachis* oil | 3.2 | 1 | 91% | 4 |
| Sunflower oil | 3.0 | 1.5 | 132% | 4 |
| Olive oil | 4.3 | 1 | 127% | 4 |
| CMC-water | 11.6 | 0.5 | 166% | 9 |
| Propylene glycol | 16.5 | 0.75 | 193% | 3 |

N: Total number of monkeys per formulation

It appears that inecalcitol was better absorbed from LCT (arachis oil, sunflower oil, olive oil) than from MCT (FIG. 1; Table 1). Long-chain fatty acid like oleic acid, the majority fatty acid esterified in the olive oil triglycerides, changed the course of inecalcitol absorption by delaying and slightly increasing its peak concentration (FIG. 2; Table 1).

It also appears that solution of inecalcitol in propylene glycol was even more readily absorbed to give rise to peak values more than 15-fold higher than from in MCI. The resulting total bioavailability was nearly doubled (FIG. 3; Table 1). However, the monoester of propylene glycol with caprylic acid (CapmulPG8®) increased inecalcitol peak plasma concentration only by a factor of 2, for an increase in bioavailability limited to about 20% (FIG. 2; Table 1).

Even more striking, when inecalcitol was administrated to monkeys in suspension in a water solution of the hydrophilic linking/disintegrating excipient carboxymethylcellulose (CMC), the absorption was better than from any solution of inecalcitol in any lipid-based excipient. Peak concentration was almost 12-fold higher with suspensions in CMC solutions than with solution in MCT. The overall bioavailability was increased by 66% (FIG. 4; Table 1).

EXAMPLE 2

Composition of 2 mg Inecalcitol Tablets

| Component | Composition centesimal (%) | Unit composition (mg) |
|---|---|---|
| Inecalcitol | 1.333 | 2.000 |
| Lactose monohydrate | 66.967 | 100.451 |
| Cellulose microcristalline ph102 | 11.000 | 16.500 |
| Carboxymethyl cellulose sodique | 3.333 | 5.000 |
| Crospovidone | 15.000 | 22.500 |
| Anhydrous collidal silicon dioxide | 0.500 | 0.750 |
| Dry vitamin E 50% | 1.667 | 2.501 |
| Magnesium stearate | 0.200 | 0.300 |
| Total raw tablet | 100.000 | 150.002 |
| Opadry II white 85F18422 | | 3.000 |
| Total coated tablet | | 153.002 |

What is claimed is:

1. An oral formulation wherein said formulation is a dry formulation which comprises:
   at least one 14-epi-analogue of vitamin D in a concentration of between 0.001 and 50% (weight),
   carboxymethylcellulose in a concentration between 0.1% and 50% (weight), and
   one or more optional pharmaceutically acceptable excipient(s)
   wherein said 14-epi-analogue of vitamin D is inecalcitol and wherein the formulation is characterized by an improved absorption profile over the medium chain triglycerides formulation of said 14-epi-analogue of vitamin D.

2. The oral formulation according to claim 1 in a unit dose.

3. The oral formulation according to claim 1 in the form of a tablet, a pill, powder, a hard capsule, a pastille, a troche, a lozenge.

4. The oral formulation according to claim 1 which further comprises a binder, a diluent, a disintegrant, a lubricant, a glidant, an antioxidant, a sweetening agent or a flavoring agent.

5. The oral formulation according to claim 1, comprising from 0.5 to 20 mg of said 14-epi-analogue of vitamin D.

6. The oral formulation according to claim 1, wherein it is characterized by a higher Cmax than the corresponding formulation in medium chain triglycerides.

7. The oral formulation according to claim 6 in a unit dose.

8. The oral formulation according to claim 6 in the form of a tablet, a pill, powder, a hard capsule, a pastille, a troche, a lozenge.

9. The oral formulation according to claim 6, which further comprises a binder, a diluent, a disintegrant, a lubricant, a glidant, an antioxidant, a sweetening agent or a flavoring agent.

10. The oral formulation according to claim 6, comprising from 0.5 to 20 mg of said 14-epi-analogue of vitamin D.

11. The oral formulation according to claim 1, wherein the formulation is characterized by a higher AUC0-24 h than the corresponding formulation in medium chain triglycerides.

12. The oral formulation according to claim 11 in a unit dose.

13. The oral formulation according to claim 11 in the form of a tablet, a pill, powder, a hard capsule, a pastille, a troche, a lozenge.

14. The oral formulation according to claim 11 which further comprises a binder, a diluent, a disintegrant, a lubricant, a glidant, an antioxidant, a sweetening agent or a flavoring agent.

15. The oral formulation according to claim 11, comprising from 0.5 to 20 mg of said 14-epi-analogue of vitamin D.

16. The oral formulation according to claim 6, wherein the formulation is characterized by a higher AUC0-24 h than the corresponding formulation in medium chain triglycerides.

17. The oral formulation according to claim 16 in a unit dose.

18. The oral formulation according to claim 16 in the form of a tablet, a pill, powder, a hard capsule, a pastille, a troche, a lozenge.

19. The oral formulation according to claim 16 which further comprises a binder, a diluent, a disintegrant, a lubricant, a glidant, an antioxidant, a sweetening agent or a flavoring agent.

20. The oral formulation according to claim 16, comprising from 0.5 to 20 mg of said 14-epi-analogue of vitamin D.

21. A method for treating rickets, osteoporosis, osteomalacia, psoriasis, multiple sclerosis or type I diabetes, hyperparathyroidism, or benign prostate hyperplasia comprising administering a formulation according to claim 1 to a human or animal patient in need thereof, wherein treating does not include preventing.

22. A method for preventing rickets, osteoporosis or osteomalacia comprising administering a formulation according to claim 1 to a human or animal patient in need thereof.

23. A method for improving the absorption of 14-epi-analogue of vitamin D over the formulation in medium chain triglyceride comprising administering a formulation according to claim 1 to a human or animal patient in need thereof, wherein the method is characterized by a higher AUC0-24 h than the corresponding formulation in medium chain triglycerides.

24. A method for treating a cancer selected from the group consisting of breast cancer, prostate cancer, lung cancer, colorectal cancer, bladder cancer, brain cancer, stomach cancer, kidney cancer, liver cancer, ovary cancer, mouth cancer, skin cancer, intestine cancer, uterine cancer, head and neck cancer and throat cancer, blood cancers, thyroid cancer, pancreatic cancer, acute myeloid leukemia and chronic lymphocytic leukemia comprising administering a formulation according to claim 1 to a human or animal patient in need thereof, wherein treating does not include preventing.

25. A method for improving the absorption of 14-epi-analogue of vitamin D over the formulation in medium chain triglyceride comprising administering a formulation according to claim 1 to a human or animal patient in need thereof, wherein the method is characterized by a higher Cmax than the corresponding formulation in medium chain triglycerides.

26. The method according to claim 25, wherein the method is also characterized by a higher AUC0-24 h than the corresponding formulation in medium chain triglycerides.

27. A method for treating rickets, osteoporosis, osteomalacia, psoriasis, multiple sclerosis or type I diabetes, hyperparathyroidism or benign prostate hyperplasia comprising administering a formulation according to claim 6 to a human or animal patient in need thereof, wherein treating does not include preventing.

28. A method for preventing rickets, osteoporosis or osteomalacia comprising administering a formulation according to claim 6 to a human or animal patient in need thereof.

29. A method for treating a cancer selected from the group consisting of breast cancer, prostate cancer, lung cancer, colorectal cancer, bladder cancer, brain cancer, stomach cancer, kidney cancer, liver cancer, ovary cancer, mouth cancer, skin cancer, intestine cancer, uterine cancer, head and neck cancer and throat cancer, blood cancers, thyroid cancer, pancreatic cancer, acute myeloid leukemia and chronic lymphocytic leukemia comprising administering a formulation according to claim 6 to a human or animal patient in need thereof, wherein treating does not include preventing.

30. A method for treating rickets, osteoporosis, osteomalacia, psoriasis, multiple sclerosis or type I diabetes, hyperparathyroidism or benign prostate hyperplasia comprising administering a formulation according to claim 11 to a human or animal patient in need thereof, wherein treating does not include preventing.

31. A method for preventing rickets, osteoporosis or osteomalacia comprising administering a formulation according to claim 11 to a human or animal patient in need thereof.

32. A method for treating a cancer selected from the group consisting of breast cancer, prostate cancer, lung cancer, colorectal cancer, bladder cancer, brain cancer, stomach cancer, kidney cancer, liver cancer, ovary cancer, mouth cancer, skin cancer, intestine cancer, uterine cancer, head and neck cancer and throat cancer, blood cancers, thyroid cancer, pancreatic cancer, acute myeloid leukemia and chronic lymphocytic leukemia comprising administering a formulation according to claim 11 to a human or animal patient in need thereof, wherein treating does not include preventing.

33. A method for treating rickets, osteoporosis, osteomalacia, psoriasis, autoimmune diseases such as multiple sclerosis or type I diabetes, hyperparathyroidism or benign prostate hyperplasia comprising administering a formulation according to claim 16 to a human or animal patient in need thereof, wherein treating does not include preventing.

34. A method for preventing rickets, osteoporosis or osteomalacia comprising administering a formulation according to claim 16 to a human or animal patient in need thereof.

35. A method for treating a cancer selected from the group consisting of breast cancer, prostate cancer, lung cancer, colorectal cancer, bladder cancer, brain cancer, stomach cancer, kidney cancer, liver cancer, ovary cancer, mouth cancer, skin cancer, intestine cancer, uterine cancer, head and neck cancer and throat cancer, blood cancers, thyroid cancer, pancreatic cancer, acute myeloid leukemia and chronic lymphocytic leukemia comprising administering a formulation according to claim 16 to a human or animal patient in need thereof, wherein treating does not include preventing.

* * * * *